United States Patent [19]

Rogers et al.

[11] Patent Number: 5,256,544
[45] Date of Patent: Oct. 26, 1993

[54] MICROBIAL SOLUBILIZATION OF PHOSPHATE

[75] Inventors: Robert D. Rogers; James H. Wolfram, both of Idaho Falls, Id.

[73] Assignee: EG&G Idaho, Inc., Idaho Falls, Id.

[21] Appl. No.: 826,563

[22] Filed: Jan. 27, 1992

[51] Int. Cl.$^5$ .......................... C12R 1/01; C12R 1/645; C12P 3/00; C12P 39/00

[52] U.S. Cl. ........................................ 435/42; 435/168; 435/813; 435/824; 435/911; 435/933

[58] Field of Search ................. 435/168, 42, 824, 933, 435/911, 813

[56] References Cited

U.S. PATENT DOCUMENTS 5,026,417  6/1991  Kucey ................................. 435/254

OTHER PUBLICATIONS

Louw et al Jove of App Bact vol. 22 pp. 227–233 (1959).
Singh et al Rev. Ecol Biol Sci vol. 19 pp. 17–25 (1982).
Kucey Canadian Jour Soil Sci vol. 63 pp. 671–678 (1983).
Singh et al Current Sci vol. 53 pp. 1212–1213 (1984).

Primary Examiner—Herbert J. Lilling
Attorney, Agent, or Firm—Alan D. Kirsch

[57] ABSTRACT

A process is provided for solubilizing phosphate from phosphate containing ore by treatment with microorganisms which comprises forming an aqueous mixture of phosphate ore, microorganisms operable for solubilizing phosphate from the phosphate ore and maintaining the aqueous mixture for a period of time and under conditions operable to effect the microbial solubilization process. An aqueous solution containing soluble phosphorous can be separated from the reacted mixture by precipitation, solvent extraction, selective membrane, exchange resin or gravity methods to recover phosphate from the aqueous solution.

11 Claims, 4 Drawing Sheets

MICROBIAL SOLUBILIZATION OF PHOSPHATE

CONTRACTUAL ORIGIN OF THE INVENTION

The United States Government has rights in this invention pursuant to Contract No. DE-AC07-76ID01570 between the U.S. Department of Energy and EG&G Idaho, Inc.

BACKGROUND OF THE INVENTION

The present invention relates to a continuous bioprocess for the solubilization of phosphate from ore containing phosphate.

Because soluble phosphate rapidly becomes insoluble during contact with soil solutions and solids and is also immobilized by biochemical processes, phosphate is a non-recoverable, irreplaceable element for plant nutrition and industrial applications. It therefore is necessary to mine phosphate, process it into a soluble form, and routinely reapply it to soil as a fertilizer. The principal markets for phosphate include the fertilizer industry and the production of elemental phosphorous which is used in the chemical and food industries. There are no existing substitutes for phosphate in these designated uses. The uses of phosphate preclude it from being recycled and therefore the supply of phosphate must continually be replenished through the process of mining and purification. It is estimated that approximately 35 million metric tons of phosphate containing ore will be processed each year.

Presently two methods for processing phosphate ($PO_4$) from phosphate containing apatite ore, or rock, are utilized, viz.: (a) the phosphoric acid wet process and (b) the phosphoric acid oxidation process The energy requirements for these two processes are approximately 9.57 MBtu/ton and 16.04 MBtu/ton of ore respectively. The most energy intensive part of the process is the separation of phosphate from apatite ore. Depending on the method used, this portion of the process demands 54% to 78% of the total processing energy. The wet process furnishes approximately 75% of the phosphoric acid produced in the United States while approximately 25% of the phosphoric acid is produced by the oxidation method. Because of the purity requirements, elemental phosphorous is typically produced by means of the more energy intensive oxidation process. Furthermore, the wet process uses large quantities of sulfuric acid for phosphate fertilizer production at a cost in excess of 3 billion dollars per year and results in the generation of substantial quantities of hazardous waste which are regulated under the Resource Conservation and Recovery Act. Treatment and disposal of these hazardous wastes involve a significant expense to the phosphate manufacturing industry and these costs are ultimately borne by the consumers. A biological processing approach for extracting phosphate from phosphate containing ore offers a less expensive and less energy intensive means than existing processes for the production of phosphoric acid.

Biological separation technology is presently being exploited with much success in the non-ferrous mining industry for the leaching of low grade copper, gold and uranium sulfide ores. Additionally, the microbial immobilization of solubilized phosphorous is shown by U.S. Pat. No. 3,980,557, Yall et al., and U.S. Pat. No. 4,220,527, Udaka et al., which disclose methods for removing soluble phosphorous from waste water using microorganisms. However, neither the processes used for sulfide ore or those described by Yall and Udaka, addresses the solubilization of phosphate from a material containing insoluble forms of phosphate, as does the present invention.

It has been shown that as a result of chemical precipitation and biological immobilization, without periodic replacement the accessible supply of phosphate in soil would rapidly be depleted. This would be the case if it were not for the occurrence of biological and chemical phosphate releasing mechanisms in soil. Microbial solubilization of soil phosphate was demonstrated and shown to enhance plant growth by Gerretson, F. C., *The Influence of Microorganisms on the Phosphate Intake by the Plant, Plant and Soil*, vol. 1, pp. 51-81, 1948. To date however, this phenomenon has only been used in situ in soils or batch shake flask experiments and not developed into a continuous process. Because of the known future need for phosphate and the evidence of susceptibility to microbial alteration, phosphate ore is an ideal candidate for a continuous bioseparation process.

It is known that microbes will solubilize phosphate from such sources as dicalcium and tricalcium phosphate, hydroxyapatite, basic slag and rock phosphate. Microorganisms possessing the ability to solubilize phosphate include bacteria, fungi and actinomycetes, and the range of phosphate solubilization ability within such a heterogeneous group is very large. The simpler calcium phosphate compounds appear to be more susceptible to microbial attack than phosphate contained in complex matrices. Studies report that over 50% of the phosphate in dicalcium and tricalcium (TCP) forms can be released by microbes growing in solution while only 1-33% of the phosphate contained in rock phosphate is released. (Louw et al., *A Study of Soil Bacteria Dissolving Certain Mineral Phosphate Fertilizers and Related Compounds*, Journal of Applied Bacteria, vol. 22, pp. 227-233, 1959; Singh et al., *Solubilization of Insoluble Phosphates by Mesophilic Fungi*, Rev. Ecol. Biological Science, vol. 19, pp. 17-25, 1982; Kucey, *Phosphate-Solubilizing Bacterial and Fungi in Various Cultivated and Virgin Alberta Soils*, Canadian, Journal of Soil Science, vol. 63, pp. 671-678, 1983; and Singh el al., *Solubilization of Rock Phosphated by Phosphate Solubilizers in Broth*, Current Science, vol. 53, pp. 1212-1213, 1984). However, Applicant has found in batch shake tests that over 90% of TCP can be solubilized with as much as 85% solubilization of rock phosphate. Applicant has also demonstrated this same enhanced degree of solubilization with an increased concentration of ore under continuous bioprocess conditions.

In addition to using a biological system in the phosphate ore process stream to supplement or replace the present extraction methodologies, such a system could also be used to extract phosphate from waste phosphate ore. By current industrial standards, ore containing less than 26% phosphorous (as $P_2O_5$) is considered waste. Typically this waste is stock piled and used as back-fill material at spent mining pits. The microbial process of the present invention would enable the further refinement of this type of material. The microbial process of the present invention can also be used to remove trace or nuisance amounts of phosphate from iron ores and other metal oxides ores, thereby facilitating the processing of the metallic ores. Furthermore, an in situ field-leaching process for recovery of phosphorous can be accomplished using the bioprocess of the present invention.

It is an object of this invention to provide a continuous biotechnical method for the industrial phosphate recovery process for the economical removal of phosphate from rock phosphate.

It is another object of this invention to provide a biotechnical method for an industrial phosphate recovery process for the removal of phosphate from low grade phosphate ore and waste material containing phosphate.

It is a further object of this invention to provide an in situ bioseparation phosphate recovery process.

It is still a further object of this invention to provide a biotechnical method for the removal of nuisance amounts of $PO_4$ from iron ores and other metal oxide ores.

Additional objects, advantages and novel features of the invention will become apparent to those skilled in the art upon examination of the following and by practice of the invention.

SUMMARY OF THE INVENTION

This process separates insoluble phosphate from an ore body utilizing biocatalysis and microbiological produced solutions. This process can be applied to phosphate rich ore where recovery of phosphate for commercial use is the intended purpose or it can be applied to other nonmineral ore matrices that contain recalcitrant trace amounts of phosphate, such as some oxide ores or waste material. Over 850 microorganisms have been studied to assess their ability to solubilize phosphate from insoluble forms of phosphate containing rock and ores. Isolates were evaluated for the ability to solubilize phosphate using an agar plate bioassay and shake flask studies.

Accordingly, there is provided a process for separating insoluble phosphate from an ore body comprising (i) ore containing phosphorous, (ii) microorganisms operable for solubilizing the insoluble phosphate, (iii) separation of the soluble phosphate from the residual solid material, and (iv) precipitating and filtering the soluble phosphate from the lixiviant, and (v) adjusting the pH of the lixiviant for recycling to the process.

One embodiment of the present invention comprises producing the microorganism in an aerobic environment by inoculating an aqueous growth medium with an inoculating amount of the microorganism thereby forming a growth mixture, maintaining the growth mixture under aerobic conditions operable to substantially increase the population of the microorganisms; and introducing the thusly produced microorganisms in a feedstream into an aqueous solution of rock phosphate.

In a further embodiment, the microorganisms are selected from the group consisting of the bacterium *Pseudemonas cepacia*, or the fungi *Aspergillus niger, Aspergillus phenicis, Penicillium herquei, Penicillium funiculosum, Penicillium lanoso-coerulum, Penicillium simlicissum, Penicillium atramentosum, Penicillium roguefortii, Paecilomyces* sp., *Acrmonium* sp., *Verticillium* sp., *Geomyces* sp., *Chrysoporium* sp., and mixed cultures of the aforementioned organisms. In a further embodiment, the microorganisms are strains of organisms which have been selected or naturally mutated so that the strains have enhanced phosphate solubilizing properties. In one embodiment, the organisms which are mutated or selected, are selected from the group consisting of the above-mentioned microorganisms.

In still a further embodiment, the phosphorous constituent which has been reduced to phosphate is soluble in the aqueous phase of the aqueous mixture, and the aqueous phase containing the soluble phosphate is separated from the mixture, and the phosphate containing precipitate is formed and separated from the thusly separated phase. In a further embodiment the aqueous phase which comprises the soluble phosphate is treated thorough a cation exchange resin bed and reintroduced into the aqueous solution of rock phosphate. Still a further embodiment of the present invention is to adjust the pH of the lixiviant for recycling in the microorganism production and subsequent steps of the biosolubilization process.

DETAILED DESCRIPTION OF THE INVENTION

Figure 1:
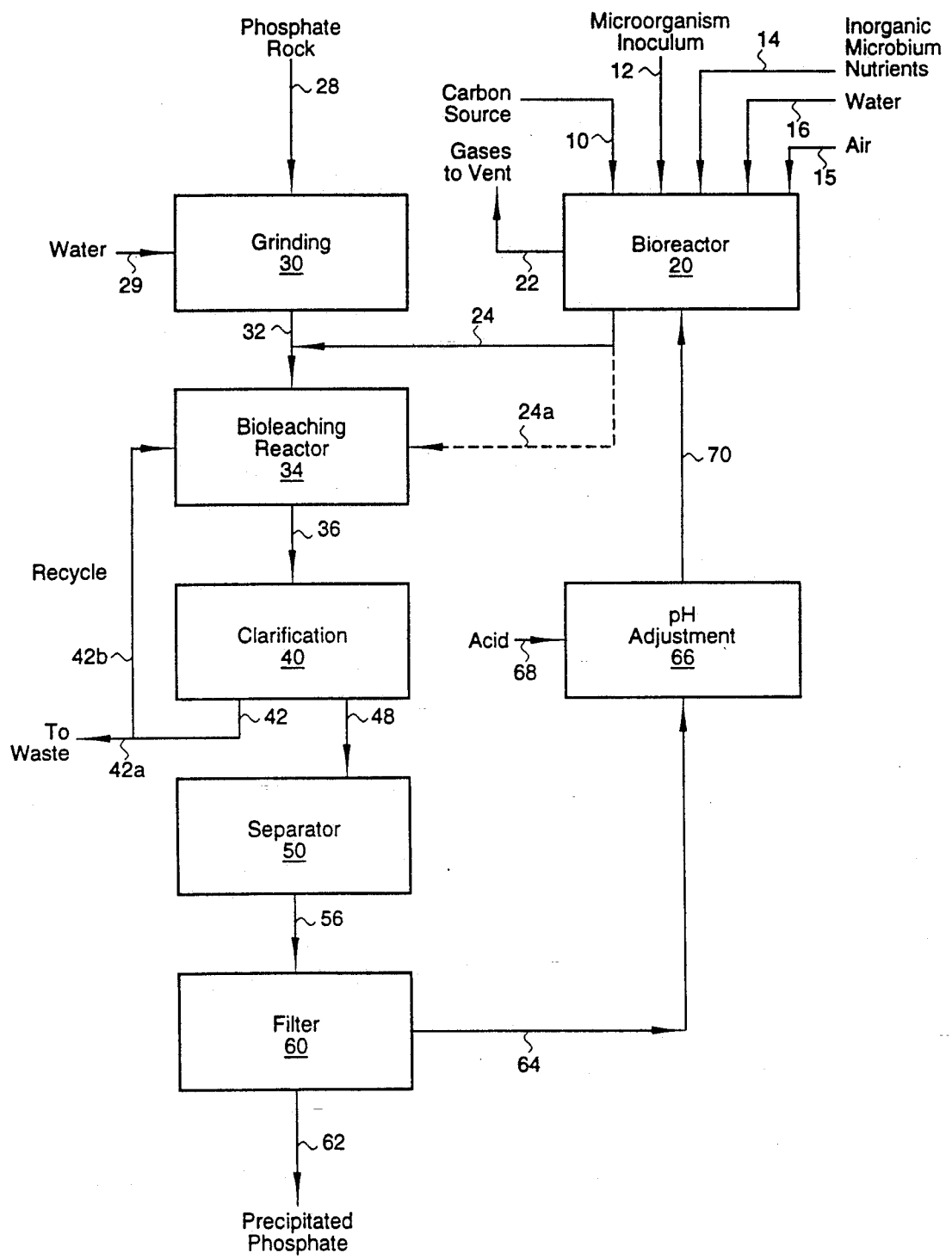
FIG. 1 is a flow diagram of a preferred embodiment of the overall process of the present invention.

In FIG. 1, a flow diagram illustrates a preferred embodiment of the overall process of the present invention. As shown in FIG. 1, microorganism production takes place in a bioreactor 20 which provides conditions conducive for the continuous growth of the microorganism. Preferably the bioreactor 20 consists of a reactor tank with a motor driven impeller, heating/cooling probe, pH probe as well as several access ports. Continuous growing conditions are initiated by microbial inoculum 12 and maintained by the steady state addition of sterile growth media to the reactor, shown in FIG. 1 as inorganic nutrients 10 and carbon source 11. Additionally, microorganism growing conditions are maintained by the control of carbon source 10, inorganic microbium nutrients 14, air supply 15, and water 16 temperatures. Possible carbon sources include such carbohydrates as glucose, sucrose and starch, organic acids, alcohol, hydrocarbons and any other materials that can be consumed by microorganisms as nourishment. A preferred carbon source of the present invention is glucose. It was found that the initiation of growth and the amount of $PO_4$ solubilized when ethanol is the source lags behind that observed when the microorganisms are grown with glucose.

In a preferred embodiment of the present invention, the inorganic microbium nutrients 14 is a glucose (1%) minimal salts media (GMSM) consisting of the following quantities of salts per liter or solution: $(NH_4)_2SO_4$ (2 g); $MgCl_2.6H_2O$ (0.3 g); $MnCl_2.4H_2O$ (0.001 g); $FeSO_4.7H_2O$ (0.0006 g); $NaMoO_4.2H_2O$ (0.026 g); and $KH_2PO_4$ (0.0035 g). Inoculation 12 involves the preparation of starter cultures using microorganisms that are pregrown with GMSM. These starter cultures are incubated for several days to allow for sufficient production of biomass. From these cultures bacterial and fungal inoculum can be prepared. Bacterial inoculum is prepared by collecting the biomass by centrifugation. The resulting pellet is then resuspended in a sterile solution of NaCl and subsequently recollected by centrifugation. The fungal inoculum is allowed to grow and produce biomass in the form of floating spheres, which are then collected and allowed to incubate for several days before their contents are harvested by centrifugation, as previously described. Water 16 and air 15 are supplied to the bioreactor 20 to provide an aerobic environment for the microorganisms. As shown in FIG. 1 gases are vented 22 from the bioreactor 20 to avoid unacceptable pressure build up which can be detrimental to the microorganisms. An aqueous solution 24 containing the microorganisms exits the bioreactor 20 which will then be introduced into an aqueous phosphate mixture.

Phosphate rock 28, which includes any ore that contains even trace amounts phosphate, undergoes a reduction of size in the grinding step 30 shown in FIG. 1. Grinding 30 is an optional step which may be omitted, depending upon the initial size of the rock phosphate. Applicant has found the rock phosphate reduced to a size of between 20 and 400 mesh is preferred. Particles larger than these ranges can be used but subsequent microbial reductions may be delayed. Particles smaller than these ranges can also be used, but the cost of the grinding operation will be increased. Water 29 is introduced in the grinding stage 30 to provide an aqueous solution of rock phosphate 32, to which said aqueous microorganism solution 24 is mixed. The mixture containing the aqueous solution of rock phosphate 32 and the aqueous microorganism solution 24 is then infused into a bioleaching reactor 34. If, as a result of having adequately sized rock phosphate the grinding step 30 is found not to be necessary, the aqueous microorganism solution stream from bioreactor 20 may be mixed with the rock phosphate solution directly in the bioleaching reactor 34 as depicted by the optional aqueous microorganism solution stream 24a of FIG. 1.

The bioleaching reactor 34 is preferably a well-mixed, continuous stirred flow reactor, however, trough reactors, fluidized bed, and column reactors are also possible. The aqueous slurry in bioleaching reactor 34 is maintained under constant agitation to prevent settling of the solids contained therein and to ensure good contact between the phosphate ore particles, and the microorganisms, thereby eliminating transport limitations to the phosphate solubilization rate.

A portion of the well-mixed contents of bioleaching reactor 34 are continuously removed therefrom in stream 36 and charged to a gravity clarifier 40 wherein settling particles are separated via gravity and unsettled inorganic particulate matter, biomass, and the entire liquid phase are separated and charged to separator 50 via stream 48. Large, predominately inorganic solids settled in clarifier 40 may be recycled via streams 42 and 42b or may be discarded as waste in stream 42a. For enhancing the solubilization process in bioleaching reactor 34, a cartridge containing cation exchange resin can be placed in the recycle feed line 42b connecting the clarifier 40 to the leach reactor 34 for the purpose of removing excess soluble calcium.

Separator 50 is preferably a precipitator wherein $Ca(OH)_2$ is used to form the phosphate precipitate. Alternatively the separator 50 could employ an organic solvent extraction process, membrane separation, gravity, or an anion exchange resin to separate the phosphate. Stream 56 then exits separator 50 and enters the filtering stage 60 which filters precipitated $PO_4$ and allows for recycling of the remaining solution into the microbial process via recycling stream 64. A pH adjustment 66 is made to recycle stream 64 by adding an acid as a reagent. After pH adjustment 66, stream 70 is then reintroduce into the bioreactor 20 and the subsequent microbial solubilization process. Phosphate solubilized by the microbial process exits filtering stage 60 via stream 62, as depicted in FIG. 1.

For a better understanding of the present invention, the following specific examples illustrate the invention.

EXPERIMENTAL STUDIES

Bioreactor studies were conducted in liquid minimal media as previously described with glucose being the source of carbon. Microorganisms being cultured in the bioreactors were also supplied with supplemental $PO_4$ (5.9 mg $PO_4$/L as $KH_2PO_4$). The source of insoluble $PO_4$ was 200 mesh rock phosphate. The microorganisms used in this study were the bacterium *Pseudomonas cepacia* and the fungus *Penicillium funiculosum*.

Prototype bioreactors used for microorganism propagation consisted of a stirred tank type and a column air lift. The bioreactors provide conditions for the continuous growth of the microorganisms with a resultant production of biochemically derived compounds. These compounds could then be provided under steady flow conditions to secondary biocontact reactors containing the phosphate rock. This arrangement allowed for the study of phosphate rock solubilization under either steady state or varying conditions.

In this study, the stirred tank bioreactor was used for propagation of the bacteria while the fungus was grown in the column. A 2-L capacity laboratory fermenter was used as the stirred tank reactor which consisted of a reactor tank with a motor driven impeller, heating/cooling probe, pH probe, as well as several access ports. The bioreactor unit was self sterilizing. Continuous growing conditions were maintained through the steady state addition of sterile growth media to the reactor. The subsequent $PO_4$ bearing liquid was collected for analysis. Results from such studies show that up to 85% of the ore can be solubilized at a continuous rate of at least 5 mEq $PO_4$/L of lixiviant. In other studies conducted by Applicant, effluent (lixiviant) from the bioreactors was distributed to various prototype biocontact reactors and columns containing phosphate ore.

The column air lift reactor used for the propagation of the fungus consisted of a 90 cm section of a 7 cm ID polycarbonate tube. The bottom of the column was sealed and contained an inlet for fresh media. A removable closure with a filtered air inlet was fitted to the top of the column and attached on the inside to an aerator at the bottom of the column. An effluent outflow port was placed near the top of the column. Suspended inside the column from top to bottom was a "ring lace" material consisting of several main nylon strings supporting an abundance of fine loops branching from the main support. The purpose of this material was to provide surface area to support the growth of the fungus. The column with the packing had a liquid volume of approximately 3 L. The column was sterilized before use and sterile growth media and fungal inoculum was added to the column and sterile air flowing bottom up was used to both agitate and aerate the liquid media. Growth media was the same as that used in the above described bacteria study except that the concentration of glucose and $KH_2PO_4$ were halved. The fungus was allowed to grow for seven days without the addition of fresh media. A slow flow of media was initiated on the seventh day and effluent was collected over the next 14 days. During the first 12 days of operation the effluent pH varied between 2.33 and 2.28 which is indicative of the presence of organic acids. However, laboratory analysis revealed an apparent absence of organic acids. To test for the presence of a phosphate ore solubilizing factor, 50 mL aliquots of the column effluent were mixed with either 100 or 250 mg of phosphate ore in a 125 Erlenmeyer flask. These flasks were incubated on a shaker for seven days. Results from this study indicate that the effluent was capable of solubilizing approximately 26% of the available PO₄ from the 100 mg sample and about 10% from the 250 mg sample.

Figure 2:
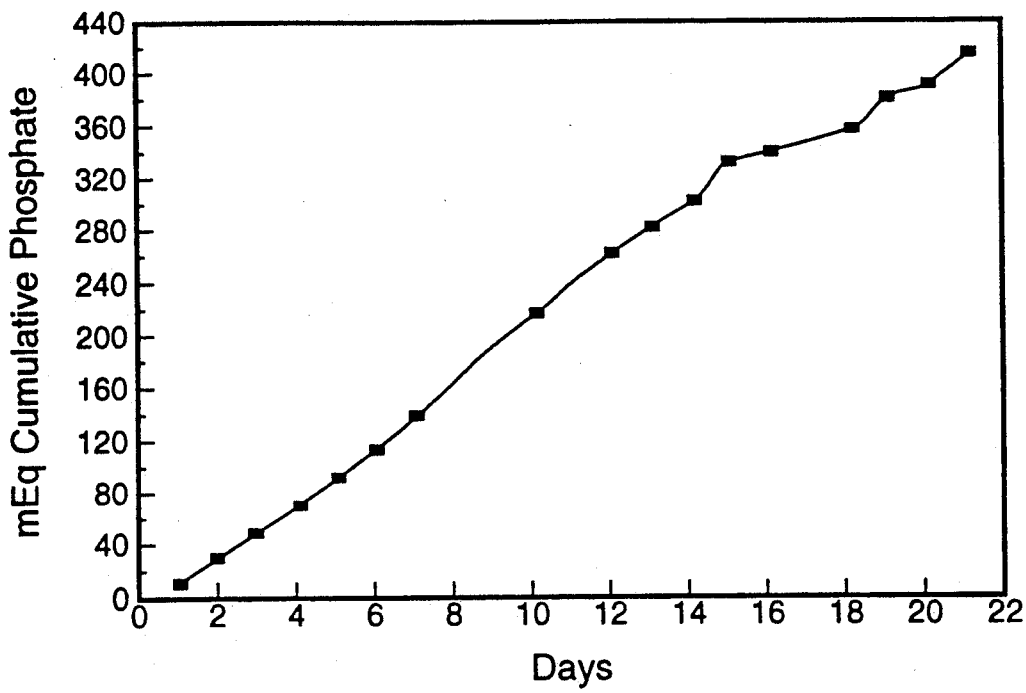
FIG. 2 through 5 are graphs showing the cumulative phosphate solubilized as a function of time in the microbial reactions.

Studies were conducted with stirred tank contact reactors and column (packed bed) reactors. In the present invention, the contact reactors are depicted in FIG. 1 as the bioleaching reactor 34. Both the stirred tank and the column were conducted with the same quantities of ore and lixiviant flow rate. The phosphate ore used in these studies contained 24.05% $P_2O_5$ (10.16 mEq $PO_4$/g) and 24.6% Ca. In one stirred tank study, 250 g (10% pulp density) of 20 mesh phosphate ore was used. The working volume of the bioreactor was maintained at 2.5 L with a lixiviant flow rate of 5 L/day. Over the period of 21 days approximately 414 mEq of PO₄ was solubilized (16.3% of that available) at a rate of 4.7 mEq PO₄/L of lixiviant. The results of this study are shown in FIG. 2.

Figure 3:
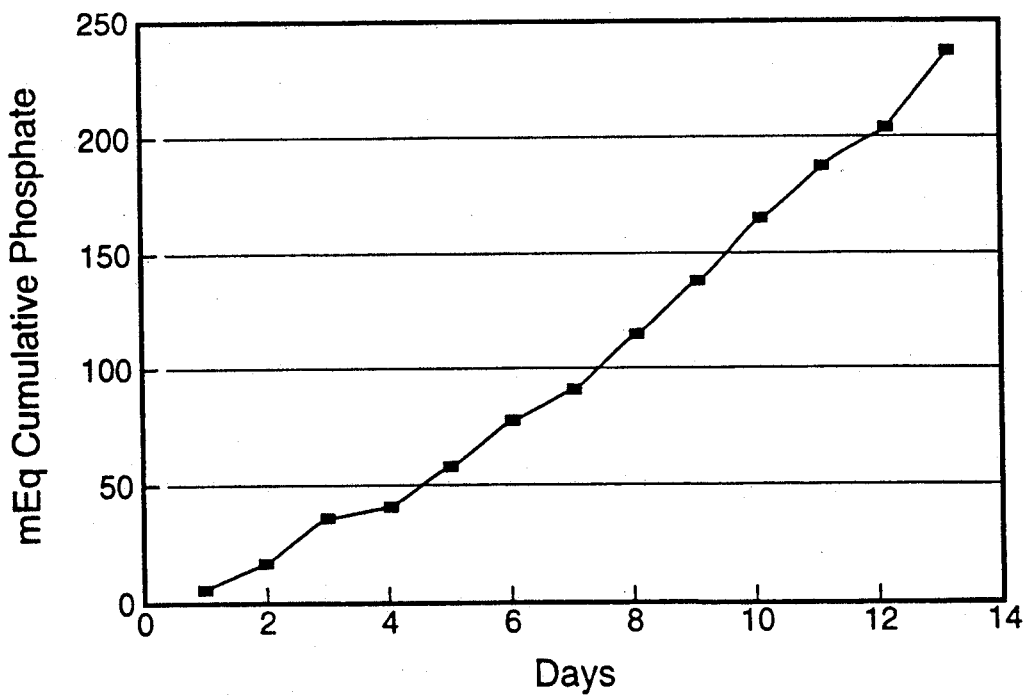

Another study was conducted using the same conditions as above, except that the size of the phosphate ore was reduced to minus 200 mesh. As shown in FIG. 3, similar results were obtained with 236 mEq of PO₄ (9.3% solubilization) solubilized in 13 days at a rate of 4.8 mEq of PO₄/L. Data from these contact reactor studies indicates that a more coarse grade of phosphate ore could be used in the microbial process, thereby resulting in a savings in energy costs related to phosphate ore size reduction.

Figure 4:
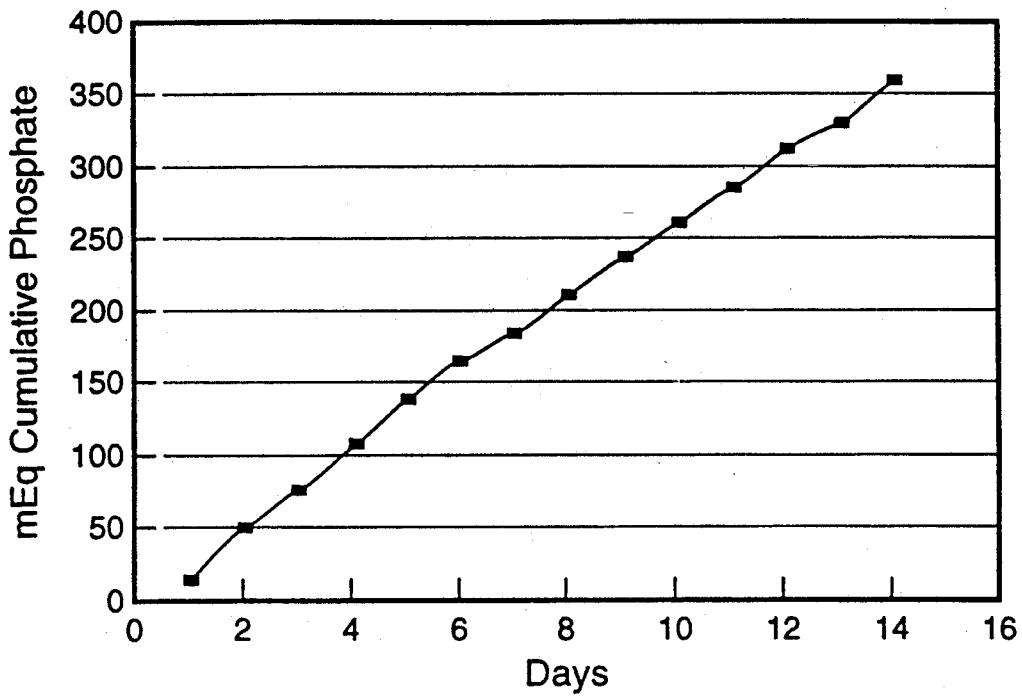

Column (packed bed) contact reactor studies were conducted wherein 1.4 kg of the phosphate rock previously described was mixed with quartz sand at a ratio of 50/50 and then place into 4 L columns. A down-flow of lixiviant at an initial rate of 3 L/day was established. Solubilization of the PO₄ at a rate of approximately 6.2 mEq of PO₄/L was maintained for approximately 13 days at which time the exposed surface of the solids became covered with a mat of biomass which inhibited lixiviant flow. Another column contact reactor study was performed in a 2.54 cm by 91.4 cm column with the lixiviant being fed in an up-flow stream (i.e., through the column bottom) rather than a down-flow as previously studied. Pea gravel (approximately 0.6 cm diameter) was placed in the bottom of the column to disperse the flow of lixiviant and encourage biomass growth on this coarser medium rather than on the phosphate ore surface. The quantity of quartz sand was increased to a ratio of 25/75 in the phosphate ore/sand mixture. Under these conditions, an uninterrupted flow of lixiviant through the column was maintained. It was noted that biomass was well established in the gravel bed and in the phosphate ore/sand mixture and that the growth did not appear to impair the lixiviant flow. As shown in FIG. 4, over a period of 14 days, 14% of the PO₄ was release at a rate of 5.7 mEq/L. This rate is similar to the rate observed in the stirred tank studies and support the possibility that the bioprocess could be used for the in situ solubilization of phosphate ore.

Applicant conducted additional studies to determine if increased rates of solubilization were attainable. It is known that the solubilization of phosphate ore is controlled by an equilibrium reaction which may be written as the following equation:

$$Ca_3(PO_4)_2 + 6H = 3Ca + 2(H_3PO_4)$$

From this equation, it can be seen that the reaction (solubilization of PO₄) can be produced through the removal of free Ca. The biological solubilization of phosphate ore is believed to transpire by the biological production of organic acids which chelate free Ca thus effectively removing it from solution. Therefore, studies were conducted to determine if cation exchange resin could be used as a method to remove soluble Ca from solution thus allowing for conditions which could be conducive for increased concentration of PO₄.

Cation exchange resin used was a Bio Rad A650W-X8 resin which comes stock in the hydrogen form. The cation exchange studies were conducted using four 125 mL contact cells (CC). Contact cell No. 1 contained phosphate ore which was exposed to continuous lixiviant flow. Contact cell No. 2 contained phosphate ore, lixiviant and 35 g of the exchange resin in the hydrogen form. Contact cell Nos. 3 and 4 contained phosphate ore and phosphate ore with resin, respectively, but were not exposed to the lixiviant, instead, water adjusted to pH 3.8 (to simulate the pH of lixiviant) served as the continuous feed. This study 3 was conducted for 12 days, during which time the pH of the solution collected from CC No. 2 and CC No. 4 was consistently approximately 2. Solution form CC No. 1 started in the range of 5 to 6 and decreased to the approximately 3.5. The pH of CC No. 3 was initially in between 7.5 and 8, gradually decreasing to approximately 6.5 to 7 over the course of the study.

Figure 5:
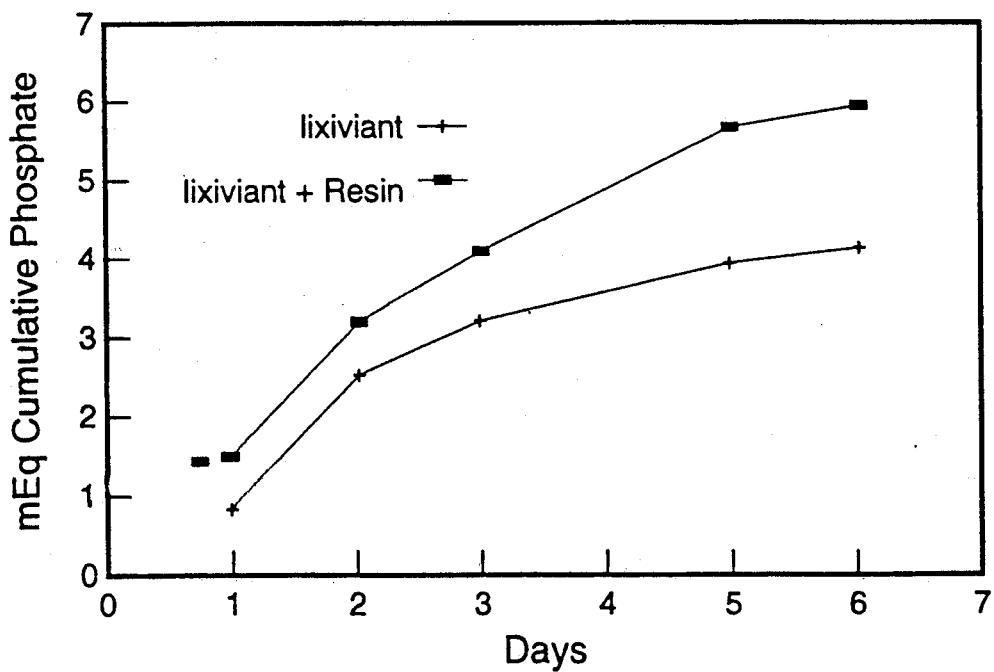

It was apparent from these data that the resin was causing the lower pH of solution in CC No. 2 and CC No. 4 because of an exchange of Ca with the sorbed hydrogen. The presence of resin had a pronounced effect on increasing the rate of PO₄ solubilization. As shown in FIG. 5, resin in combination with the biologically produced lixiviant (CC No. 2) solubilized 91% of the available PO₄ within three days at a rate of 26.14 mEq of PO₄/L solution. Following that was CC No. 4 (water and resin) which had 84% solubilization in five days at a rate of 9.77 mEq of PO₄/L. Phosphate ore exposed only to lixiviant (CC No. 1) was 59% solubilized by day 12 at a rate of 3.4 mEq of PO₄/L. That phosphate ore exposed to pH 3.8 water (CC No. 1) had only 3% of the PO₄ removed at a rate of 0.22 mEq of PO₄/L.

In another exchange resin study, conditions were the same as above, except the exchange resin was converted to a sodium (Na) form by soaking it in 500 mL of 1 N NaOH. In this study, CC No. 1 contained only phosphate and lixiviant while CC No. 2 contained phosphate ore and the Na resin that had been washed with sufficient water until the pH of the rinse water was 7.5, indicating that excess NaOH had been removed. In this study, the lixiviant in the CC No. 1 was continuously passed through a cartridge containing the exchange resin in a closed loop cycle. The closed loop was designed so as not to interfere with the constant flow of lixiviant through the contact cell. Lixiviant with a reduced Ca concentration but enriched in soluble PO₄ then be recycled back to the contact cell. The results of this study are depicted in FIG. 5 which demonstrates that the cartridge containing the Na exchange resin did promote increase solubilization of phosphate ore. As can be seen in FIG. 5, a 36% solubilization rate (3.8 mEq of $PO_4$/L) was observe in closed loop resin cartridge study of CC No. 1, versus a 25% solubilization rate (2.8 mEq of $PO_4$/L) in the lixiviant only flow in CC No. 2. The pH of the lixiviant from both contact cells remained in the range of 4 to 4.5 during the course of the study.

Figure 6:
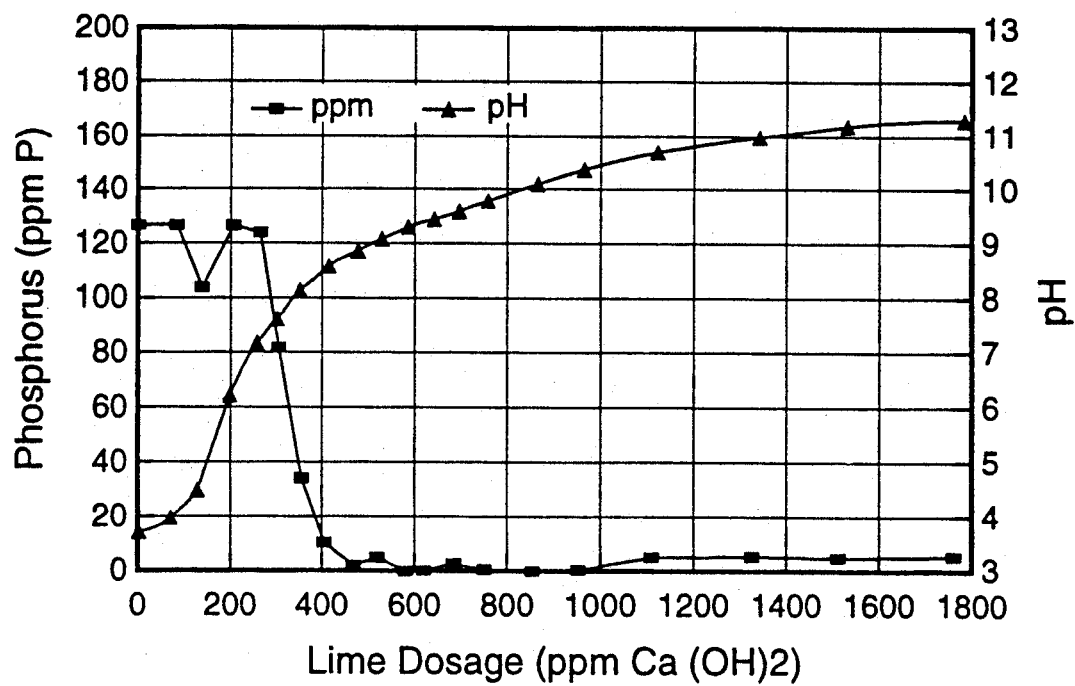
FIG. 6 is a graph illustrating the soluble phosphate precipitated as a function of pH and $Ca(OH)_2$ dosage.

Studies were also conducted on the development of a system to separate solubilized $PO_4$ from the spent lixiviant and to determine coagulation of soluble $PO_4$ using lime ($Ca(OH)_2$). Before use, solids were removed from the effluent by centrifugation. Premeasured amounts of lime were then added to a known volume of the effluent and the amount of soluble $PO_4$ and pH of the solutions were determined. As shown in FIG. 6, it was found that when the solution pH was increased to 9, the soluble $PO_4$ precipitated from solution.

The foregoing description of the preferred embodiments of the invention has been presented for purposes of illustration and description. It is not intended to be exhaustive or to limit the invention to the precise form disclosed, and obviously many modification and variations are possible in light of the above teaching. The embodiments described explain the principles of the invention and practical application and enable others skilled in the art to utilize the invention in various embodiments and with various modifications as are suited to the particular use contemplated. It is intended that the scope of the invention be defined by the claims appended hereto.

The embodiments of this invention in which an exclusive property or privilege is claimed are defined as follows:

1. A continuous bioprocess for separating insoluble phosphate from an ore body, the steps comprising:
   (a) forming phosphate ore particles;
   (b) forming an aqueous mixture which comprises (i) said phosphate ore particles formed in step (a), and (ii) an effective amount of microorganisms operable for separating said phosphate ore particles into soluble phosphate;
   (c) maintaining continuously said aqueous mixture for a predetermined period of time under conditions of temperature and pressure and under an atmospheric environment, operable for solubilizing from said phosphate ore particles at least a major part of phosphate by the microbial activity of said microorganisms;
   (d) separating said aqueous mixture into (i) an aqueous phase containing said soluble phosphate and which is substantially free of undissolved solids, and (ii) a slurry fraction which contains undissolved solids;
   (e) separating said aqueous phase containing said soluble phosphate into (i) phosphate, and (ii) an aqueous solution containing an amount of said microorganisms.

2. The process of claim 1, wherein said separating of said aqueous phase in step (e) is by precipitation, solvent extraction, selective membrane, exchange resin or gravity.

3. The process of claim 1, further comprising producing said microorganisms in an aerobic environment by inoculating an aqueous growth medium with an inoculating amount of said microorganisms thereby forming a biomass; maintaining said biomass under aerobic conditions operable to substantially increase the population of said microorganisms through the continuous introduction of nutrients; and introducing said thusly produced biomass in a continual feedstream into said aqueous mixture as said effective amount of said microorganisms mentioned in step (b).

4. The process of claim 1, further comprising the step of recycling the undissolved solids produced in step (d) into the microbial solubilization environment of step (c).

5. The process of claim 4, wherein said undissolved solids are conveyed through a cation exchange resin bed before recycling to step (c).

6. The process of claim 5, wherein said cation exchange resin bed is of a hydrogen or sodium form.

7. The process of claim 3, further comprising adjusting the pH of said aqueous solution containing an amount of said microorganisms in step (3) by a sufficient amount to reintroduce said microorganisms into step (b).

8. The process of claim 1, wherein said maintaining of said aqueous mixture in step (c) is conducted in a system which comprises a well mixed continuous flow reactor.

9. The process of claim 1, wherein said maintaining of said aqueous mixture in step (c) is conducted on phosphate ore in situ.

10. The process of claim 1, wherein said microorganisms are selected from the group consisting of *Pseudomonas cepacia, Aspergillus niger, Aspergillus phenicis, Penicillium herquei, Penicillium funiculosum, Penicillium lanoso-coerulum, Penicillium simlicissum, Penicillium atramentosum, Penicillium roguefortii, Paecilomyces* sp., *Acrmonium* sp., *Verticillium* sp., *Geomyces* sp., *Chrysoporium* sp., and mixed cultures of the aforementioned microorganisms.

11. The process of claim 1, wherein said microorganisms are strains of organisms which have been mutated of selected so that said strains have enhanced phosphate solubilizing properties, said organisms being selected from the group consisting of *Pseudomonas cepacia, Aspergillus niger, Aspergillus phenicis, Penicillium herquei, Penicillium funiculosum, Penicillium lanosocoerulum, Penicillium simlicissum, Penicillium atramentosum, Penicillium roguefortii, Paecilomyces* sp., *Acrmonium* sp., *Verticillium* sp., *Geomyces* sp., *Chrysooorium* sp., and mixed cultures of the aforementioned microorganisms.

* * * * *